United States Patent [19]

Schwarz et al.

[11] 4,298,598

[45] Nov. 3, 1981

[54] TISSUE ADHESIVE

[75] Inventors: Otto Schwarz; Yendra Linnau; Franz Löblich; Thomas Seelich, all of Vienna, Austria

[73] Assignee: Immuno Aktiengesellschaft für chemisch-medizinische Produkte, Vienna, Austria

[21] Appl. No.: 118,656

[22] Filed: Feb. 4, 1980

[30] Foreign Application Priority Data

Feb. 15, 1979 [AT] Austria .................................. 1190/79

[51] Int. Cl.³ ...................... A61K 35/14; A61K 37/00
[52] U.S. Cl. .................................... 424/101; 424/177
[58] Field of Search ................................ 424/101, 177

[56] References Cited
PUBLICATIONS

Matras et al., Wiener Medizinischen wochenschrift, No. 37, pp. 517–523 (1972).

Spängler et al., Wiener klinische wochenschrift, 85 (50), 827–829, (1973).
Spängler, Wiener klinische wochenschrift, Supplement 49, vol. 88, pp. 3–18 (1976).
Matras et al., Wiener klinische wochenschrift 90 (12) pp. 419–425 (Jun. 1978).
Stemburger, Thrombosis Research, vol. 12, No. 5, pp. 907–910, Pergammon Press (1978).

*Primary Examiner*—Frank Cacciapaglia, Jr.
*Attorney, Agent, or Firm*—Brumbaugh, Graves, Donohue & Raymond

[57] ABSTRACT

A tissue adhesive on the basis of human or animal proteins has a content of factor XIII and fibrinogen, the ratio of factor XIII to fibrinogen, expressed in units of factor XIII per gram of fibrinogen, amounting to at least 80. Furthermore, it contains a plasminogen-activator-inhibitor or plasmin-inhibitor in an amount of 20 to 2,000 KIU per ml.

5 Claims, No Drawings

TISSUE ADHESIVE

The invention relates to a tissue adhesive based on human or animal proteins containing factor XIII and fibrinogen.

It has long been known to use blood coagulating substances to stop bleeding and for sealing wounds. According to the first proposals of this kind, fibrin tampons and fibrin platelets, respectively, were used. During the Second World War, tissue adherence by means of blood plasma was suggested.

In recent times, a tissue adhesive based on fibrinogen and factor XIII for seamless interfascicular nerve transplantations in animal experiments has been described by H. Matras et al. in "Wiener Medizinischen Wochenschrift", 1972, page 517.

A further study was carried out by Spängler et al. in "Wiener Klinischen Wochenschrift", 1973, pages 1 to 7. Also there, the possibility was shown in animal experiments of carrying out a tissue adherence with the aid of fibrinogen as a cryoprecipitate and thrombin.

These known preparations have not yet proven to be satisfactory since they do not sufficiently meet the demands required of a tissue adhesive, i.e.

(a) a high straining capacity of the adherences and wound sealings as well as safe and permanent blood stopping, i.e. good adhering capacity of the adhesive to the wound and tissue surfaces, as well as high internal strength of the same, (b) controllable durability of the adherences in the body, (c) complete absorbability of the adhesive in the course of the wound healing process, (d) properties which stimulate wound healing. This may partly be due to the fact that, in the known preparations, the coagulation factors necessary for stopping bleeding have not been present in an optimal proportion to one another, and also to the fact that the fibrinolytic activity in the area of adherence has not been sufficiently under control. Premature dissolutions of the tissue adherences frequently occurred due to enzymatic influence.

The invention is aimed at avoiding these disadvantages and difficulties and has as its object to provide a tissue adhesive on the basis of fibrinogen and factor XIII of human or animal origin, which adhesive meets the requirements initially set out.

The invention is based on the finding that it is necessary to provide a certain ratio of fibrinogen to factor XIII and that the fibrinolytic activity is inhibited by a certain amount of an inhibitor.

Accordingly, the invention consists in a combination of the following characteristic features:

(a) that the ratio of factor XIII to fibrinogen, expressed in units of factor XIII per gram of fibrinogen, amounts to at least 80, (b) that a plasminogen-activator-inhibitor or plasmin-inhibitor, preferably aprotinin, is contained in an amount of 20 to 2000 Kallikrein-inactivator-units (KIU) per ml.

According to a preferred embodiment, the tissue adhesive contains cold-insoluble globulin, which, increases the efficiency.

According to a further characteristic feature of the invention, the tissue adhesive also contains albumin, which exerts a stabilizing effect on the components of the tissue adhesive.

According to a preferred embodiment, fibrinogen, cold-insoluble globulin and albumin are contained at a ratio of 60 to 98: 0.5 to 20: 0 to 15, and factor XIII is contained in an amount of at least 7 units/ml.

In order to guarantee the desired effect, fibrinogen is present in an amount of at least 70 mg/ml.

The tissue adhesive according to the invention possesses characteristic cross-linking properties, which are determined according to the sodium-dodecyl-sulphate-(SDS)-polyacrylamide-gel-electrophoresis method, K. Weber and M. Osborn. The Reliability of Molecular Weight Determinations by Dodecyl Sulfate-Polyacrylamide Gel Electrophoresis. J.Biol.Chem. 244, 16, pp. 4406–4412 (1969); M. L. Schwartz et al. The Effect of Fibrin Stabilizing Factor on the Subunit Structure of Human Fibrin. J. of Clin. Invest. 50, p. 1506–1513 (1971). After mixing of the tissue adhesive with an equal volume of a solution containing 40 $\mu$Moles of $CaCl_2$ and 15 NIH-units (U.S. National Institute of Health-units) of thrombin per ml, the mixture is incubated at 37° C. The cross-linking degree is determined by gel electrophoresis after stopping the reaction and reductive splitting of the disulphide bridges contained in the proteins by the addition of a mixture of urea, sodium dodecyl sulphate and $\beta$-mercaptoethanol. Typical of the tissue adhesive according to the invention is a complete cross-linking of the fibrin-$\gamma$-chains after 3 to 5 minutes, and a cross-linking of at least 35% of the fibrin-$\alpha$-chains after 2 hours.

The invention furthermore comprises a method of producing the tissue adhesive described by starting out from human or animal plasma cryoprecipitate. The method is characterized in that cold-soluble plasma-protein is removed from the cryoprecipitate by a single or repeated treatment with a buffer solution containing sodium citrate, sodium chloride, glycine, glucose and a plasminogen-activator-inhibitor or plasmin inhibitor, and the purified precipitate is dissolved.

Advantageously, the cryoprecipitate has been produced from fresh human or animal plasma frozen at −20° C. When increasing the temperature to 0° to 2° C., the cryoprecipitate is gained and separated by centrifugation. The buffer solution by which the cryoprecipitate is treated is to have a pH of 6.0 to 8.0. The cold-soluble plasma protein is separated by centrifugation on maintaining a temperature of 0° to 4° C. The purified precipitate is then washed with the buffer solution until the desired ratio of factor XIII to fibrinogen and the desired proportions of fibrinogen, cold-insoluble globulin and albumin are reached.

The purified precipitate dissolved can be preserved by deepfreezing.

The tissue adhesive according to the invention can be applied universally. It can be used for the seamless connections of human or animal tissue or organ parts, for sealing wounds and stopping bleedings as well as for the stimulation of wound healing.

Preferred fields of application, in which the tissue adhesive according to the invention can be successfully used, are: in the field of ear, nose and throat surgery, oral surgery, dentistry, neurosurgery, plastic surgery, general surgery, abdominal surgery, thorax and vascular surgery, orthopaedics, urology, ophthalmology and gynaecology.

Advantageously, a mixture of thrombin and calcium chloride is added to the adhesive prior to the application of the tissue adhesive according to the invention or is applied onto the tissues to be connected.

The method of the invention will be explained in more detail by the following example 1:

178.5 l of human fresh plasma deep-frozen at −20° C. were heated to +2° C. The cryoprecipitate obtained was separated by centrifugation and treated at +2° C. with 8 l of a buffer solution containing 6.6 g of $Na_2$-citrate.$0.2H_2O$, 3.4 g of NaCl, 10.0 g of glycine, 13.0 g of glucose.$1H_2O$ and 50,000 KIU of aprotinin per liter, and having a pH of 6.5, and was again centrifuged at +2° C. The treatment with the buffer solution mentioned and the subsequent centrifugation were repeated once. The separated precipitate was liquefied by heating to 37° C.

Aprotinin was present in the product thus obtained in a concentration of 50 KIU per ml. The ratio of fibrinogen to cold-insoluble globulin to albumin in the product was determined to be 86.2:6.7:2.2. This determination was carried out also by the SDS-polyacrylamide-gel-electrophoresis method, i.e. (a) with a non-reduced sample of the tissue adhesive and (b) with a sample reduced with β-mercaptoethanol. 13.8 units/ml of factor XIII were found and the ratio of factor XIII to fibrinogen, expressed in units of factor XIII per gram of fibrinogen, was 152. Fibrinogen was present in an amount of 90.6 mg/ml.

The determinations were carried out in the following manner: The determinations of the factor-XIII-units was performed by means of a cross-linking test in which factor-XIII-free fibrinogen was used as a substrate and the fibrin-cross-linking caused by the addition of the unknown diluted sample served as a measure for the amount of factor XIII contained therein. A corresponding calibration curve was obtained with pooled human citrate plasma, 1 ml plasma containing 1 unit of factor XIII per definitionem. The protein determinations were carried out by the method according to Kjeldahl.

The cross-linking test according to the SDS-polyacrylamide-gel-electrophoresis method showed complete fibrin-γ-cross-linking after 5 minutes and 68% fibrin-α-cross-linking after 2 hours. The end product was put into final containers and deepfrozen at −20° C. for storage.

According to a modified method, it is also possible to add the plasminogen-activator-inhibitor or plasmin inhibitor at a later stage, as will be illustrated by the following example 2:

112.5 l of human fresh plasma deepfrozen at −20° C. were heated to +2° C. The resulting cryoprecipitate was separated by centrifugation and washed at +2° C. with 10 l of a buffer solution containing 6.6 g of $Na_3$-citrate.$0.2H_2O$, 3.4 g of NaCl, 10.0 g of glycine, 13.0 g of glucose.$1H_2O$ per liter, and having a pH of 6.5, and was again centrifuged at +2° C. The separated precipitate was liquefied by heating to 37° C. 50 KIU of aprotinin per ml were added to the solution thus obtained.

In the product thus obtained the ratio of fibrinogen to cold-insoluble globulin to albumin was determined to be 91.0:5.3:1.1. This determination was carried out also by the SDS-polyacrylamide-gel-electrophoresis method, i.e. (a) with a non-reduced sample of the tissue adhesive, and (b) with a sample reduced with β-mercaptoethanol. 15.7 units/ml of factor XIII were found and the ratio of factor XIII to fibrinogen, expressed in units of factor XIII per gram of fibrinogen, was 170. Fibrinogen was present in an amount of 92.1 mg/ml.

The determinations were carried out in the following manner: The determination of the factor-XIII-units was performed by means of a cross-linking test in which factor-XIII-free fibrinogen was used as a substrate and the fibrin-cross-linking caused by the addition of the unknown diluted sample served as a measure for the amount of factor XIII contained therein. A corresponding calibration curve was obtained with pooled human citrate plasma, 1 ml plasma containing 1 unit of factor XIII per definitionem. The protein determinations were carried out by the method according to Kjeldahl.

The cross-linking test according to the SDS-polyacrylamide-gel-electrophoresis method showed complete fibrin-γ-cross-linking after 5 minutes and 87% fibrin-α-cross-linking after two hours. The end product was put into one-way injection syringes and deepfrozen at −20° C. for storage.

What we claim is:

1. A tissue adhesive comprising plasma proteins of human or animal origin, which plasma proteins contain: factor XIII in an amount of at least 7 units/ml, fibrinogen in an amount of at least 70 mg/ml, the ratio of factor XIII to fibrinogen, expressed in units of factor XIII per gram of fibrinogen, amounting to at least 100; cold-insoluble globulin and albumin, the ratio of fibrinogen to cold-insoluble globulin to albumin being 60 to 98: 0.5 to 20: 0 to 15; aprotinin in an amount of 20 to 2,000 KIU per ml, wherein the tissue adhesive as determined according to the SDS-polyacrylamide-gel-electrophoresis method is capable of complete cross-linking of the fibrin-γ-chains after 3 to 5 minutes of incubation and of at least 35% cross-linking of the fibrin-α-chains after two hours of incubation.

2. A method of producing a tissue adhesive as described in claim 1, which comprises:
   (a) thawing deep frozen fresh plasma to obtain a cryoprecipitate and a soluble plasma protein;
   (b) separating the cryoprecipitate from the soluble plasma protein;
   (c) washing the thus obtained cryoprecipitate at about 2° C. with a buffer solution having a pH of about 6.5 and containing sodium citrate, sodium chloride, glycine, glucose and a plasminogen-activator inhibitor or a plasmin inhibitor;
   (d) heating the washed precipitate to about 37° C. to obtain a liquid tissue adhesive; and
   (e) deep-freezing the liquid tissue adhesive until ready to use.

3. A method of producing a tissue adhesive as described in claim 1 which comprises the steps of:
   (a) thawing deep-frozen fresh plasma to obtain a cryoprecipitate and soluble plasma protein;
   (b) separating the cryoprecipitate from the soluble plasma protein;
   (c) washing the thus obtained cryoprecipitate at about 2° C. with a buffer solution having a pH of about 6.5 and containing sodium citrate, sodium chloride, glycine and glucose;
   (d) heating the washed precipitate to about 37° C. to obtain a liquid tissue adhesive; and
   (e) deep-freezing the liquid tissue adhesive until ready to use.

4. A method of tissue or organ adhesion in mammals which comprises applying onto the organ or tissue an amount sufficient to function as an adhesive of the adhesive as described in claim 1 and a mixture of thrombin and calcium chloride.

5. The method of claim 1, wherein the mixture of thrombin and calcium chloride is added to the adhesive prior to applying the tissue adhesive to the tissue or organ.

* * * * *

UNITED STATES PATENT AND TRADEMARK OFFICE
CERTIFICATE OF CORRECTION

PATENT NO. : 4,298,598

DATED : Nov. 3, 1981

INVENTOR(S) : Schwarz et al.

It is certified that error appears in the above—identified patent and that said Letters Patent is hereby corrected as shown below:

Col. 1, line 26, "(a) a high" should read --(a) high--;

Col. 4, line 64, "claim 1" should read --claim 4--.

Signed and Sealed this

Ninth Day of March 1982

[SEAL]

Attest:

GERALD J. MOSSINGHOFF

Attesting Officer     Commissioner of Patents and Trademarks